(12) United States Patent
Ellis (10) Patent No.: US 7,955,260 B2
(45) Date of Patent: Jun. 7, 2011

(54) METHOD FOR RATING SEVERITY OF PSORIASIS

(75) Inventor: Charles N. Ellis, Ann Arbor, MI (US)

(73) Assignee: DatAcquire, Inc., Ann Arbor, MI (US)

( * ) Notice: Subject to any disclaimer, the term of this patent is extended or adjusted under 35 U.S.C. 154(b) by 1756 days.

(21) Appl. No.: 10/530,003

(22) PCT Filed: Oct. 20, 2003

(86) PCT No.: PCT/US03/33218
§ 371 (c)(1),
(2), (4) Date: Mar. 31, 2005

(87) PCT Pub. No.: WO2004/034888
PCT Pub. Date: Apr. 29, 2004

(65) Prior Publication Data
US 2005/0228235 A1 Oct. 13, 2005

Related U.S. Application Data (60) Provisional application No. 60/419,652, filed on Oct. 18, 2002.

(51) Int. Cl.
*A61B 5/00* (2006.01)
(52) U.S. Cl. ..................................................... 600/306
(58) Field of Classification Search .................. 600/300, 600/301, 306; 128/898, 920; 705/2–4
See application file for complete search history.

(56) References Cited

U.S. PATENT DOCUMENTS

| | | | |
|---|---|---|---|
| 6,021,344 A | 2/2000 | Lui et al. | |
| 6,159,445 A | 12/2000 | Klaveness et al. | |
| 6,269,818 B1 | 8/2001 | Lui et al. | |
| 6,436,127 B1 | 8/2002 | Anderson et al. | |

OTHER PUBLICATIONS

International search report for PCT application No. PCT/US2003/033218.
Marks, R., et al., Assessment of disease progress in psoriasis, Arch Dermatol, vol. 125(2): pp. 235-240, 1989.
McKenna, K.E., et al., The outcomes movement and new measures of the severity of psoriasis, J. Am. Acad. Dermatol., vol. 34(3): pp. 534-538, 1996.
Ashcroft, D.M., et al.,Clinical measures of disease severity and outcome in psoriasis: a critical appraisal of their quality, Br. J. Dermatol., vol. 141(2): pp. 185-191, 1999.
Bigby, M., et al., Understanding and evaluating clinical trials, J. Am. Acad. Dermatol., vol. 34: pp. 555-590, 1996.
Fredriksson, T., et al., Severe psoriasis—oral therapy with a new retinoid, Dermatologica, vol. 157(4): pp. 238-244, 1978.
Griffiths, C. E. M., et al., A Photonumeric Scale for the Assessment of Cutaneous Photodamage, Arch Dermatol, vol. 128: pp. 347-351, Mar., 1992.

(Continued)

*Primary Examiner* — Charles A Marmor, II
(74) *Attorney, Agent, or Firm* — Calfee, Halter & Griswold LLP (57) ABSTRACT

Methods for rating the severity of psoriasis in a patient are provided. Such methods comprise assessing the percent of the patient's body surface exhibiting signs of psoriasis, assessing the overall elevation, erythema, and scale of the patient's psoriasis plaques, and classifying the severity of the patient's psoriasis into at least four classes based upon the percent of the patient's body surface exhibiting signs of psoriasis adjusted by the overall elevation, erythema and scale of the patient's psoriasis plaques. In the present methods the weight given to one or more of the overall qualities of elevation, erythema or scale of the patient's psoriasis plaques in classifying the severity of the patient's psoriasis into a higher class is greater than the weight given to other of the overall qualities. A computer readable medium and system for practicing the present methods are also provided.

45 Claims, 2 Drawing Sheets

OTHER PUBLICATIONS

Office Action, dated Jan. 13, 2010, issued by The United States Patent and Trademark Office in related U.S. Appl. No. 11/222,518.

Response, filed Apr. 13, 2010, to Office Action, dated Jan. 13, 2010, issued by The United States Patent and Trademark Office in related U.S. Appl. No. 11/222,518.

Office Action, dated Jul. 13, 2010, issued by the U.S. Patent and Trademark Office in related U.S. Appl. No. 11/222,518.

Office Action, dated Feb. 3, 2011, issued by the U.S. Patent and Trademark Office in related U.S. Appl. No. 11/222,518.

Supplementary European Search Report for EP Patent Application No. 03777712.5, dated Mar. 16, 2011.

Bruce et al., Comparative study of calcipotriene (MC 903) ointment and fluocinonide ointment in the treatment of psoriasis, Journal of American Academy of Dermatology, vol. 31, No. 5, Part 1, pp. 755-759, Nov. 1994.

Ellis et al., A Randomized Comparative Study of Psoriasis Area and Serverity Index, Psoriasis Global Assessment, and Lattice System-Global Psoriasis Core in rating psoriasis, Journal of Investigative Dermatology, vol. 121, No. 1, p. 355, Jul. 2003.

Langley et al., Evaluating psoriasis with Psoriasis Area and Severity Index, Psoriasis Global Assessment, and Lattice System Physician's Global Assessment, Journal of American Academy of Dermatology, vol. 51, No. 4, pp. 563-569, Oct. 1, 2004.

METHOD FOR RATING SEVERITY OF PSORIASIS

This application claims the benefit of the filing date of U.S. Provisional Application No. 60/419,652, filed Oct. 18, 2002 which, in its entirety, is incorporated herein by reference.

TECHNICAL FIELD OF THE INVENTION

The present invention relates to methods of rating the severity of psoriasis in a subject, more particularly a human patient.

BACKGROUND

Psoriasis is a debilitating autoimmune dermatological disease that affects about 2.6% of the population. Plaque psoriasis, the most common form of the disease, is characterized by red skin covered with silvery scales. Histologically the picture is one of disordered differentation and hyperproliferation of keratinocytes within the psoriatic plaque with inflammatory cell infiltrates.

Onset occurs most often in early adult life, but also may begin in childhood or in aged people. Severity of the disease varies and is usually characterized by alternating periods of remission and flare-up. In more serious cases, psoriasis can affect up to 90% of the skin and can be life threatening.

New therapeutic agents are currently being developed to treat this skin disorder. Accurate, reliable, and appropriate documentation of the extent and severity of psoriasis is important in clinical practice, and essential for clinical trial research. In clinical trials, the objective quantification of the disease is critical to measure the efficacy of an investigational treatment by comparing the severity of disease before therapy to that measured after treatment. For a new therapy to achieve regulatory approval for marketing, its efficacy must be documented in clinical trials. Valid and reliable outcome measures are also important in evidence-based medicine to provide comparisons among similarly designed trials in the literature. Although outcome measures such as quality-of-life assessments are important methods of assessing patient morbidity and disease severity, the clinical evaluation of psoriasis severity currently is the primary efficacy variable in clinical trial research.

Despite the importance of psoriasis evaluation, there is a lack of consensus on the most appropriate measure.[1-4] The measures most often employed in clinical trials to measure psoriasis disease severity are the Psoriasis Area and Severity Index (PASI) and the Psoriasis Global Assessment (PGA). PASI was developed in 1978 by Fredricksson and Pettersson[5] for use in a single clinical trial. Subsequently, the PASI became popular as a research tool, but is not used in clinical practice. The PASI results in a single score for psoriasis severity from 0 to 72; the plaque qualities of erythema, infiltration, desquamation are weighted equally to each other in calculating the final score. The method for calculating such score is depicted in Table 1 below.

TABLE 1

Method for calculating the Psoriasis Area and Severity Index (PASI)
The original description of the PASI involves the assessment over 4 body regions (head, trunk, upper and lower extremities) of infiltration, desquamation, and erythema, and body surface area involvement. The assessment for infiltration, desquamation, and erythema use a 5-point scale:

| | |
|---|---|
| No symptoms | 0 |
| Slight | 1 |
| Moderate | 2 |

TABLE 1-continued

Method for calculating the Psoriasis Area and Severity Index (PASI)
The original description of the PASI involves the assessment over 4 body regions (head, trunk, upper and lower extremities) of infiltration, desquamation, and erythema, and body surface area involvement. The assessment for infiltration, desquamation, and erythema use a 5-point scale:

| | |
|---|---|
| Marked | 3 |
| Very marked | 4 |
| Based on the extent of lesions in each anatomic region, the area affected is assigned a numerical value of 1 to 6: | |
| <10% of the body surface involved (per region) | 1 |
| 10-29% | 2 |
| 30-49% | 3 |
| 50-69% | 4 |
| 70-89% | 5 |
| 90-100% | 6 |

Since the head, upper extremities, trunk, and lower extremities, correspond to approximately 10, 20, 30, and 40% of body surface area, respectively, the PASI score can be calculated using the formula:
$$PASI = 0.1 (E_h + I_h + D_h)A_h + 0.2(E_u + I_u + D_u)A_u + 0.3(E_t + I_t + D_t)A_t + 0.4(E_l + I_l + D_l)A_l$$
where E, I, D, and A denote the point score for erythema, infiltration, desquamation, and area, respectively, and h, u, t, and l denote head, upper extremities, trunk, and lower extremities, respectively. PASI varies in steps 0.1 units from 0.0 to 72.0, with the highest score representing near or complete body involvement with the most severe erythema, infiltration, and desquamation possible.

The PGA allows the investigator to assign a single estimate of the patient's overall severity of disease; typically, a 7-point scale from clear to severe is used, although many variations have been employed. The PGA evaluates disease severity in a more intuitive and clinically meaningful way than does the 0 to 72 score of the PASI. In most versions of the PGA, the individual elements of psoriasis plaque morphology or degree of body surface area involvement are not quantified. A detailed description of one PGA method is depicted in Table 2 below.

TABLE 2

Description of a Physician's Global Assessment (PGA)

| | |
|---|---|
| Severe | Very marked plaque elevation, scaling, and/or erythema |
| Moderate to severe | Marked plaque elevation, scaling, and/or erythema |
| Moderate | Moderate plaque elevation, scaling, and/or erythema |
| Mild to moderate | Intermediate between moderate and mild |
| Mild | Slight scaling plaque elevation, scaling, and/or erythema |
| Almost clear | Intermediate between mild and clear |
| Clear | No signs of psoriasis (post-inflammatory hyperpigmentation may be present) |

The reliability of current clinical outcome measures is uncertain. Accordingly, new methods for rating the severity of psoriasis are needed.

SUMMARY OF THE INVENTION

Figure 1:
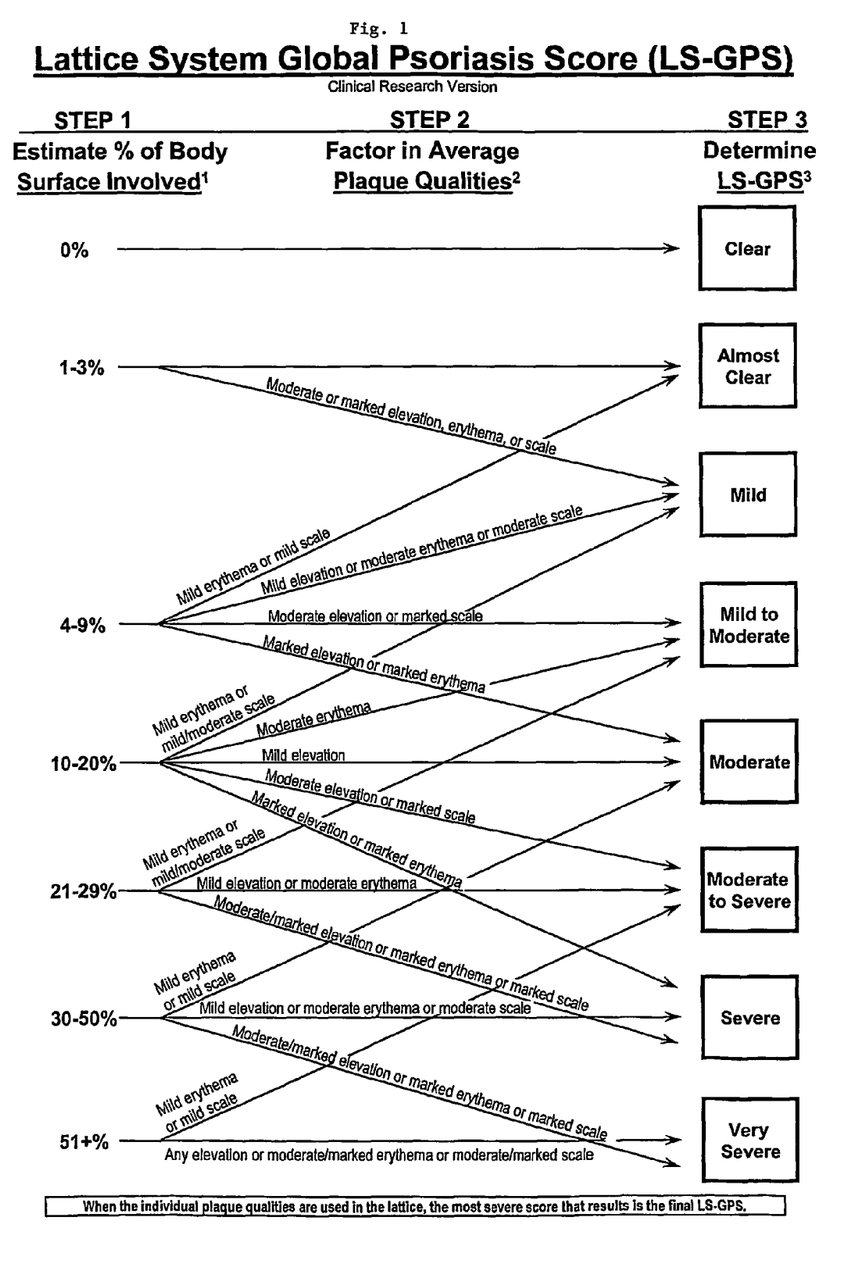
FIG. 1 is a graphic representation of one embodiment of the present method, referred to hereinafter as the Lattice System Global Psoriasis Score-1 (LS-GPS-1). The method comprises two steps. In the first step, the percentage of body surface involved is assessed using a 7-point scale. In the second step, average plaque qualities of elevation, erythema, and scaling are assessed using a 4-point scale. Then scores for percentage of body surface and average plaque qualities are combined in a Lattice to determine an 8-point score from clear to very severe.
Figure 2:
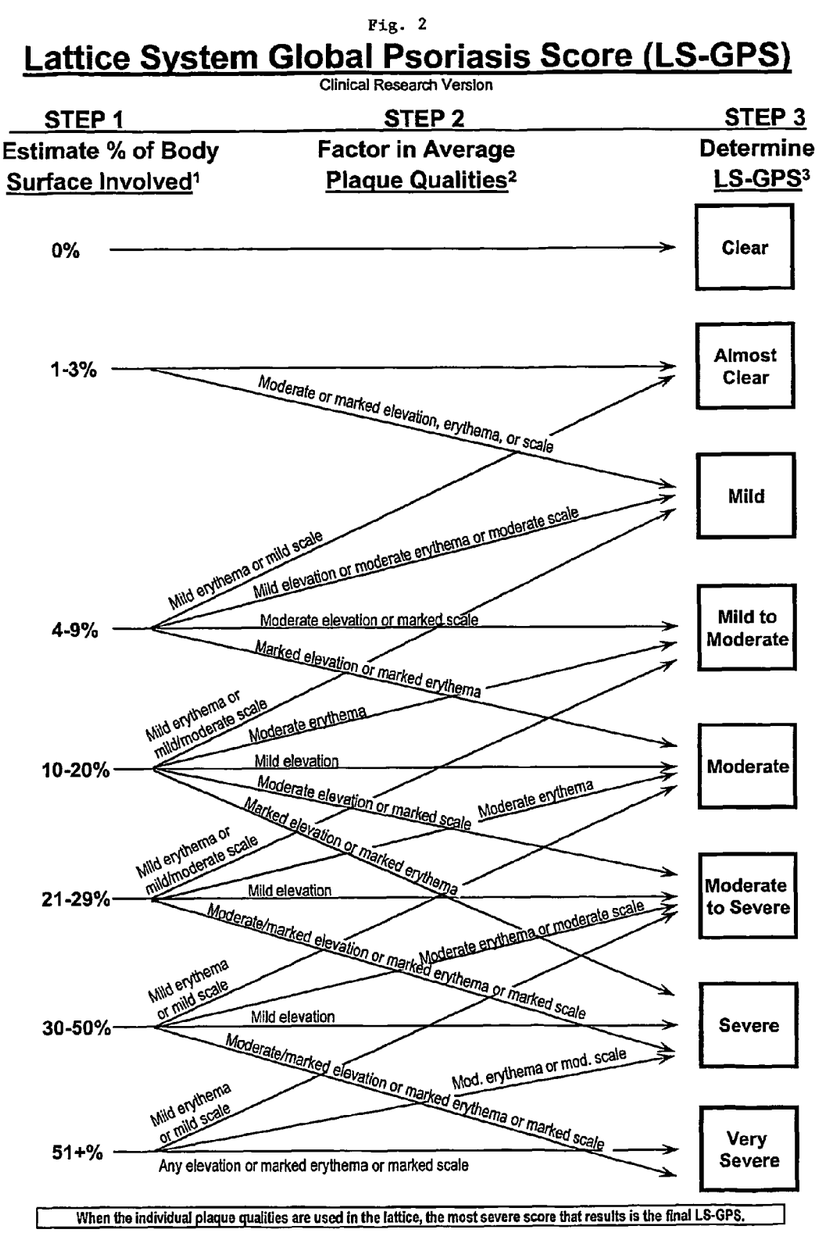
FIG. 2 is a graphic representation of one embodiment of the present method, referred to hereinafter as the Lattice System Global Psoriasis Score-2 (LS-GPS-2). The method comprises two steps. In the first step, the percentage of body surface involved is assessed using a 7-point scale. In the second step, average plaque qualities of elevation, erythema, and scaling are assessed using a 4-point scale. Then scores for percentage of body surface and average plaque qualities are combined in a Lattice to determine an 8-point score from clear to very severe.

The present invention provides methods for rating the severity of psoriasis. Such methods comprise determining a global score of the severity of the disease. In one part, the score is based on the percentage of body surface showing signs of psoriasis. Such signs include increased elevation, erythema, and scale. Although it is possible to examine the head, neck, chest, back, abdomen, groin, buttocks, and both arms and both legs (including hands and feet) of the patient separately or in groupings such as the trunk (chest, back, and abdomen), it is preferred that the entire body be examined to assess such percentage. The global score is also based on the overall elevation, overall erythema, and overall scale of the psoriasis plaques in all the involved areas. The overall elevation of the plaques in the involved areas is given added weight in determining the global score, and, preferably, the overall level of scale is given a lesser weight in the determination. Preferably, overall elevation, erythema, and scale are divided into a plurality of categories ranging from 0 or none up to the highest category. One example of a suitable designation for the category assessment is in four steps, namely none, mild, moderate, and marked. However, other designations may be used. Preferably the percentage of body showing signs of psoriasis is also divided into a plurality of ranges, such as, for example, 1-3%, 4-9%, 10-20%, 21-29%, 30-50%, and greater than 50%. However, other ranges may be used. The global score may be determined using a graphic system, such as shown in FIG. 1 or 2, or a software program. The global score is used to classify the severity of the patient's psoriasis into four or more classes.

The present methods are useful for evaluating the effects of therapeutic agents on psoriasis. The present methods are also useful for rating psoriasis to qualify patients for certain therapies (e.g., for insurance coverage or risk:benefit determinations).

The present invention also relates to a computer readable medium and a system for rating the severity of psoriasis in a patient in accordance with the present methods.

DETAILED DESCRIPTION OF THE INVENTION

Definitions

"Elevation" as used herein means the visually observable, palpable, or measured overall height of the plaques on the subject above normal skin. The edge characteristics of the plaques may also be used to assess the extent of elevation of the plaques.

"Erythema" as used herein means redness, or degree or quality of red color of the plaques of psoriasis or skin as measured or visually observed.

"Scale" as used herein means the amount of stratum corneum that is present on the surface of the plaques of psoriasis or skin as measured, palpated, or visually observed.

The present method provides static methods for assessing the severity of psoriasis in a patient. The method comprises assessing the percentage of the patient's body surface that exhibits signs of psoriasis, assessing the overall elevation, erythema, and scale of the areas that exhibit signs of psoriasis, and obtaining a global score of the patient's psoriasis on the basis of the percentage of the patient's body surface that exhibits signs of psoriasis adjusted by the extent of elevation, erythema and scale of the involved areas. The weight given to elevation in obtaining the global score is greater than the weight given to erythema or scale. In certain cases, the weight given erythema in obtaining the global score is greater than the weight given scale. The global score is used to classify the severity of the patient's psoriasis into four or more classes. In a preferred embodiment, the severity of the patient's psoriasis is classified into 4-10 classes. Good results have been obtained by classifying the severity of the patient's psoriasis into 8 classes.

The percentage of the patient's body surface exhibiting signs of psoriasis is measure or estimated by a qualified person. Preferably, the amount of the body surface area that is involved with psoriasis is qualified into a plurality of increasing ranges, preferably 4 to 10 ranges of increasing involvement. Good results have been obtained by grouping the percentage into the following 7 groups: 0%, 1-3%, 4-9%, 10-20%, 21-29%, 30-50% and 51-100%.

In a preferred embodiment, the severity of the overall quality of the psoriasis plaques for elevation, erythema, and scale is categorized into a plurality of categories of increasing severity with the lowest category encompassing plaques that exhibit no elevation, erythema, or scale, respectively. Preferably, elevation, erythema, and scale are categorized into 2 to 8 categories. Good results have been achieved when elevation, erythema, and scale are categorized into four categories, which in the present case are designated as none, mild, moderate, and marked, for convenience.

Preferably scale is ignored in determining the plaque elevation. In the four category system, the extent of elevation is placed in the lowest category, i.e., none, if overall there is no elevation of the psoriasis plaques above the normal skin of the patient. The extent of elevation preferably is placed in the next to lowest category, i.e. mild, if there is a slight elevation above surrounding normal skin, and the edges are typically barely palpable and not seen. The extent of elevation preferably is placed in the next to highest category, e.g. moderate, if there is a visually apparent elevation in the plaque edges, and the plaques have readily palpated edges with rounded or sloped edges. The extent of elevation preferably is placed in the highest category, e.g., marked, if there is a visually obvious elevation in the plaque edges, and the edges are easily palpated and the plaques have sharp edges that provide a discernible bump when sliding the finger from normal skin to the plaque.

In the four category embodiment, the severity of the overall quality of the psoriasis plaques for their erythema is categorized in the lowest category, e.g., none if the plaques have normal skin color or post-inflammatory color change. Erythema preferably is placed in the next to lowest category if the plaques have pink color, including "residual hyperemia" ("end of therapy hyperemia"). Erythema preferably is placed in the next to highest category, e.g., moderate if the plaques are a light to medium red color, and in the highest category, e.g. marked if the plaques are a bright, full or deep red color.

In the four category embodiment, the severity of the overall quality of the psoriasis plaques for their scale is categorized in the lowest category if there are no scales present in the involved areas, and, preferably, in the next to lowest category, e.g., mild, if fine scales looking like dust are present. The overall quality of the scales preferably is categorized in the next to highest category, e.g., moderate, if individual scales are discernible that are yellow to silver in color in the involved areas and in the highest category, e.g., marked, if the scales are coarse and thick, and yellow or silver in color, and the plaque has rough edges giving the impression that the scales could be lifted with a fingernail.

In alternative embodiments, the assessments may include thickness, induration or infiltration instead of elevation, or color or redness instead of erythema, or scaling or desquamation instead of scale. In such alternative embodiments one or a combination of these alternative assessments may be used.

Good results have been achieved employing a system that classifies the severity of the patient's psoriasis into 8 classes, characterized as "Clear", "Almost Clear", "Mild", "Mild to Moderate", "Moderate", "Moderate to Severe", "Severe", and "Very Severe". One example of such an 8 class method is shown in FIG. 1. In this system, labeled LS-PGS-1", patients with 0% involvement receive a final rating of "Clear". Patients with 1-3% involvement receive a final rating of "Almost Clear", unless they have moderate or marked elevation, erythema, or scale in which case they receive a final rating of "Mild". Patients with 4-9% involvement receive a final rating of "Almost Clear" if they have mild erythema or mild scale, unless they have mild elevation or moderate erythema or moderate scale, in which case they receive a final rating of "Mild", unless they have moderate elevation or marked scale, in which case they receive a final rating of "Mild-to-Moderate", unless they have marked elevation or marked erythema, in which case they receive a final rating of "Moderate". Patients with 10-20% involvement receive a final rating of "Mild" if they have mild erythema or mild or moderate scale, unless they have moderate erythema, in which case they receive a final rating of "Mild-to-Moderate", unless they have mild elevation, in which case they receive a final rating of "Moderate", unless they have moderate elevation or marked scale, in which case they receive a final rating of "Moderate-to-Severe", unless they have marked elevation or marked erythema, in which case they receive a final rating of "Severe". Patients with 21-29% involvement receive a final rating of "Mild-to-Moderate" if they have mild erythema or mild or moderate scale, unless they have mild elevation or moderate erythema, in which case they receive a final rating of "Moderate-to-Severe", unless they have moderate or marked elevation or marked erythema or marked scale, in which case they receive a final rating of "Severe". Patients with 30-50% involvement receive a final rating of "Moderate" if they have mild erythema or mild scale, unless they have mild elevation or moderate erythema or moderate scale, in which case they receive a final rating of "Severe", unless they have moderate or marked elevation or marked erythema or marked scale, in which case they receive a final rating of "Very Severe". Patients with over 50% involvement receive a final rating of "Moderate-to-Severe" if they have mild erythema or mild scale; otherwise they receive a final rating of "Very Severe". When such method is used, the most severe score that results is the final rating.

Another 8 class system, referred to herein as LS-GPS-2, is shown in FIG. 2. In the LS-GPS-2 system, patients with 0% involvement receive a final rating of "Clear". Patients with 1-3% involvement receive a final rating of "Almost Clear", unless they have moderate or marked elevation, erythema, or scale in which case they receive a final rating of "Mild". Patients with 4-9% involvement receive a final rating of "Almost Clear" if they have mild erythema or mild scale, unless they have mild elevation or moderate erythema or moderate scale, in which case they receive a final rating of "Mild", unless they have moderate elevation or marked scale, in which case they receive a final rating of "Mild-to-Moderate", unless they have marked elevation or marked erythema, in which case they receive a final rating of "Moderate". Patients with 10-20% involvement receive a final rating of "Mild" if they have mild erythema or mild or moderate scale, unless they have moderate erythema, in which case they receive a final rating of "Mild-to-Moderate", unless they have mild elevation, in which case they receive a final rating of "Moderate", unless they have moderate elevation or marked scale, in which case they receive a final rating of "Moderate-to-Severe", unless they have marked elevation or marked erythema, in which case they receive a final rating of "Severe". Patients with 21-29% involvement receive a final rating of "Mild-to-Moderate" if they have mild erythema or mild or moderate scale, unless they have moderate erythema, in which case they receive a final rating of "Moderate", unless they have mild elevation, in which case they receive a final rating of "Moderate-to-Severe", unless they have moderate or marked elevation or marked erythema or marked scale, in which case they receive a final rating of "Severe". Patients with 30-50% involvement receive a final rating of "Moderate" if they have mild erythema or mild scale, unless they have moderate erythema or moderate scale, in which case they receive a final rating of "Moderate to Severe", unless they have mild elevation, in which case they receive a final rating of "Severe", unless they have moderate or marked elevation or marked erythema or marked scale, in which case they receive a final rating of "Very Severe". Patients with over 50% involvement receive a final rating of "Moderate-to-Severe" if they have mild erythema or mild scale; unless they have moderate erythema or moderate scale, in which case they receive a final rating of "Severe", unless they have any elevation or marked erythema or marked scale, in which case they receive a final rating of "Very Severe". When such method is used, the most severe score that results is the final rating.

In additional embodiments, other assessments, referred to herein as "disabling findings", may be used to adjust the ratings. Such disabling findings include involvement of the face, groin, palms, soles, or axilla with psoriasis. Such disabling findings are used to increase the level of severity of the overall classification. For example, 1 to 2 levels of severity may be added to the overall rating if 1 to 2 disabling findings are present or 2 to 3 levels of severity if 2 to 5 disabling findings are present. In a further embodiment, the global score is increased by two levels of severity if plaques with elevation, scale, or erythema or a combination thereof are present on the palms, soles, or groin and by three levels of severity plaques with elevation, scale, erythema, or a combination thereof are present on the soles, palms, or groin of the patient.

In additional embodiments, the method may be simplified to make it more accessible to a wider group of raters, such as might be used by health care providers in a private practice setting.

EXAMPLES

The following example is for purposes of illustration only and is not intended to limit the scope of the invention as defined in the claims which are appended hereto. The references cited in this document are specifically incorporated herein by reference.

Example 1

Studies were conducted to quantify the relative variation in two commonly used outcome measures (the Psoriasis Area and Severity Index [PASI], and the Psoriasis Global Assessment [PGA]), and one embodiment of the present method, the Lattice System Global Psoriasis Score (LS-GPS-1).

Psoriasis rating systems can be described as static or dynamic. Static refers to scores that are not based on previous scores but rather only on findings at the time the score is rendered. Dynamic scores relate the patient's current condition to that of a previous time, usually the baseline value. Dynamic scores typically have descriptions such as "worse than at baseline", "better than at baseline", and "much better than at baseline". All three rating methods in our study are static and objective (defined as being measured by an observer).

Method

Thirty-five patients with psoriasis were recruited for the study from the outpatient department, phototherapy unit, and the Day Treatment Center of the University of Michigan Department of Dermatology. Dermatology nurses asked patients to participate with a goal to recruit a range of severity of psoriasis; patients were compensated for their time. No medications were used during the study. The patients were not participating in other research studies nor were they invited to do so as part of this project. The study was approved by the University of Michigan Health System Institutional Review Board.

Patients' ages ranged from 22 to 62 years (median 42); 66% (23/35) were men and 34% (12/35) were women. Thirty-one (89%) were Caucasian, 2 were African-American (6%), 1 was Asian (3%), and 1 was Hispanic (3%). Patients received numbers; their names were not used. Prior to beginning the study, each patient completed the Dermatology Life Quality Index questionnaire which asks patients to assess how much their skin condition affected their quality of life over the previous week.

The study was designed for each subject to be evaluated twice by each of 17 physicians, first in the morning, and, after a luncheon break, again in the afternoon. In the morning, patients were randomly assigned to examination rooms in the University of Michigan outpatient building and were re-randomized in the afternoon. No rooms had windows and all were identical in layout; all patients wore identical examination gowns. In each session, the investigators were randomly assigned a starting room and proceeded in a room-to-room sequence until all patients were evaluated with the three rating systems.

Investigators reported the number of psoriasis clinical trials in which they had used the PASI or PGA and were classified as experienced if they had previously been investigators in three or more such clinical trials. Nine (53%) of the investigators were experienced and 8 (47%) were inexperienced. Investigators' years of practicing dermatology ranged from 0 (a senior resident in dermatology) to 39 years (median 14 years for experienced investigators, 13 for inexperienced). Of the experienced investigators, 2 had participated in 4-10, 4 in 10-20, and 3 in greater than 20 clinical trials using the PASI or PGA. Training on the day of the evaluations consisted of a brief review of the methods of the three rating systems and general instructions on recording the data, lasting approximately 30 minutes. Of the expected number of evaluations (1190 for each rating method), 94 percent were completed appropriately to permit comparison of the rating systems. The investigators marked case report forms for the PGA score and each of the components of the PASI and LS-GPS; the final score for each evaluation using the latter two methods was tabulated later by computerized algorithm.

Statistical Analysis

Correlations among the three measures were evaluated by Spearman's correlation coefficients; Spearman's partial coefficients, adjusted for demographic values, were used with quality of life. Analysis of variance (ANOVA) was used to assess the variability in PASI, PGA and LS-GPS within and among individual raters, and to compare experienced and inexperienced raters. Reliability was determined overall by Cronbach's alpha coefficient and by the intra-class coefficient for agreement between the two sessions. PASI was rounded to the nearest integer.

Results

Relationships of the Rating Systems to Each Other

The Spearman correlation coefficients for all investigators for PASI and PGA (0.87), PASI and LS-GPS (0.86), and PGA and LS-GPS (0.83) indicate the measures were highly correlated. (A coefficient of 1 would indicate complete agreement of the scores whereas 0 would indicate absolutely no relationship among the scores.) These relationships were similar for both experienced and inexperienced raters for PASI and PGA (0.88 vs. 0.86 respectively), PASI and LS-GPS (0.87 vs. 0.86), and PGA and LS-GPS (0.84 vs. 0.83).

Relative Intra-Rater and Inter-Rater Variation

Table 3 summarizes the intra-rater and inter-rater variation of psoriasis assessments of PASI, PGA and LS-GPS based on an analysis of variance (ANOVA). For all investigators, low intra-rater variation occurred with the PGA (sigma=0.2) and the LS-GPS (sigma=0.5); the variation with the PASI was higher (sigma=2.5). The intra-rater variation for PASI among inexperienced investigators (sigma=3.2) was almost 3 times higher than that for experienced investigators (sigma=11.2). Thus, when using the PASI score to assess severity of psoriasis, experienced investigators were more consistent in evaluating patients at morning and afternoon sessions than were inexperienced investigators. Experience had a negligible effect on the PGA and LS-GPS (Table 3).

As expected, the inter-rater variation was greater than intra-rater variation for all rating systems. For all investigators, PASI had the highest variation (sigma=78.8) compared to PGA (sigma=31.2) and LS-GPS (sigma=1.7). Experience again reduced variation more for PASI than for PGA or LS-GPS. (Table 3).

Standard deviations about the mean scores for each patient indicate the degree of consistency across investigators in rating the patient's psoriasis. For PASI scores, experienced investigators had smaller standard deviations than did inexperienced investigators for 94 percent of the patients (data not shown). However, for PGA and LS-GPS, the ratings showed no trend for inexperienced investigators to be less consistent than experienced investigators.

TABLE 3

Inter-Rater and Intra-Rater Variability

| PSORIASIS ASSESSMENT | Intra-Rater Variation Sigma | Inter-Rater Variation Sigma |
|---|---|---|
| All Raters (N = 17) | | |
| PASI | 2.5 | 8.8 |
| PGA | 0.2 | 1.2 |
| LS-GPS | 0.5 | 1.7 |
| Experienced Raters (N = 9) | | |
| PASI | 1.2 | 8.1 |
| PGA | 0.3 | 1.2 |
| LS-GPS | 0.4 | 1.8 |

TABLE 3-continued

Inter-Rater and Intra-Rater Variability

| PSORIASIS ASSESSMENT | Intra-Rater Variation Sigma | Inter-Rater Variation Sigma |
|---|---|---|
| Inexperienced Raters (N = 8) | | |
| PASI | 3.2 | 9.6 |
| PGA | 0.3 | 1.3 |
| LS-GPS | 0.5 | 1.5 |

ANOVA test.
PASI, Psoriasis Area and Severity Index;
PGA, Physician's Global Assessment;
LS-GPS, Lattice System Global Psoriasis Score Intra-Rater Variation by Change of Assessments Between Sessions Overall reliability by Cronbach's alpha coefficient was similar for all rating systems (0.9 for each). Concordance of scores between sessions using intra-class coefficients (ICC) demonstrated highest reliability for LS-GPS (ICC=0.13). Reliability was 36 percent lower for PGA (ICC=0.08) and 49 percent lower for PASI (ICC=0.07). Among the inexperienced investigators, reliability of the PASI was particularly poor (ICC=0.04), approximately 2-fold and 4-fold poorer than for PGA and LS-GPS, respectively.

Relationship of Severity Scores to Quality of Life

None of the rating measures was correlated with patients' current quality of life (r<0.2 for each rating method).

Discussion

In this inter-rater and intra-rater variability study, the psoriasis assessments PASI, PGA, and LS-GPS were assessed twice in 35 subjects by 17 raters yielding over 3500 observations. The PASI, PGA, and LS-GPS were highly correlated with each other (r>0.8 for all comparisons).

The variation within each investigator was highest for PASI and particularly low for the PGA and LS-GPS; the latter method had the most reproducibility from session to session. As expected, the inter-rater variation was greater for all psoriasis measures; again, the PASI showed the most variability. The experience level of investigator affected consistency and reliability in the PASI, but not the PGA or LS-GPS.

Implications for Clinical Trials of Psoriasis Therapies

The greater variability seen between (inter-rater) than within (intra-rater) investigators is of importance for clinical trial research. The objective quantification of the severity of psoriasis before and after treatment is critical to measuring the efficacy of therapy. Therefore, to judge a treatment effect, the variation in rating a patient from time to time should be low; too great a variation in the rating method could interfere with determining treatment effect. If the intra-rater variability of a rating system is low, it should be reliable for the same investigator examining a given patient.

Recognizing that variability exists among investigators, however, has practical implications for conducting clinical trial research, particularly when more than one investigator may evaluate the same patient over time. Our data support the effort usually made in dermatologic trials to ensure that the same investigator conducts initial and follow-up evaluations. In instances where this is not possible, one may expect more "noise" (i.e., variability) in the clinical trial data.

REFERENCES

1. Marks R, Barton S P, Shuttleworth D, Finlay A Y. Assessment of disease progress in psoriasis. Arch Dermatol 1989; 125(2):235-40.
2. Mckenna K E, Stern R S. The outcomes movement and new measures of the severity of psoriasis. J Am Acad Dermatol 1996; 34(3):534-8.
3. Ashcroft D M, Wan Po A L, Williams H C, Griffiths C E. Clinical measures of disease severity and outcome in psoriasis: a critical appraisal of their quality. Br J Dermatol 1999; 141(2):185-91.
4. Gadenne A S, Bigby M. Understanding and evaluating clinical trials. J Am Acad Dermatol 1996; 34:555-590.
5. Fredriksson T, Pettersson U. Severe psoriasis—oral therapy with a new retinoid. Dermatologica 1978; 157(4): 238-44
6. Van de Kerkhof P C. The Psoriasis Area and Severity Index and alternative approaches for the assessment of severity: persisting areas of confusion. Br J Dermatol 1997; 137(4): 661-2.
7. Ormerod A D, Dwyer C M, Weller R, Cox D H, Price R A comparison of subjective and objective measures of reduction of psoriasis with the use of ultrasound, reflectance colorimetry, computerized video image analysis, and nitric oxide production. J Am Acad Dermatol 1997; 37(1):51-7.
8. Ramsay B, Lawrence C M. Measurement of involved surface area in patients with psoriasis. Br J Dermatol 1991; 124(6):565-70.
9. Tiling-Grosse S, Rees J. Assessment of area of involvement in skin disease: a study using schematic figure outlines. Br J Dermatol 1993; 128(1):69-74.
10. Bahmer F. The size of lesions, or point counting as a step toward the solution of the PASI problem. Arch Dermatol 1989; 125(9):1282-3.
11. Lahti A, Kopola H, Harila A, Myllyla R, Hannuksela M. Assessment of skin erythema by eye, laser Doppler flowmeter, spectroradiometer, two-channel erythema meter and Minolta chroma meter. Arch Dermatol Res 1993; 285 (5):278-82.
12. Serup J, Agner T. 72 Colorimetric quantification of erythema-a comparison of two colorimeters (Lange Micro Color and Minolta Chroma Meter CR-200) with a clinical scoring scheme and laser-Doppler flowmetry. Clin Exp Dermatol 1990; 15(4):267-72.

I claim:

1. A method for rating the severity of psoriasis in a patient, comprising:
    a) assessing a percent of the patient's body surface exhibiting signs of psoriasis,
    b) assessing overall qualities of the patient's psoriasis plaques, said qualities being elevation, erythema, and scale,
    c) classifying, in a computing device, the severity of the patient's psoriasis into at least four classes of increasing severity,
    wherein a classification into the lowest class indicates that the patient is free of psoriasis, and wherein a classification into the highest class indicates that the patient has a most severe form of psoriasis,
    wherein said classification is based upon the percent of the patient's body surface exhibiting signs of psoriasis adjusted by the overall elevation, erythema and scale of the patient's psoriasis plaques, and
    wherein the weight given to one or more of the overall qualities of elevation, erythema or scale of the patient's psoriasis plaques in classifying the severity of the patient's psoriasis into a higher class is greater than the weight given to other of the overall qualities.

2. The method of claim 1 wherein the overall elevation, erythema and scale of the patient's psoriasis plaques are categorized into a plurality of categories of increasing severity, with the lowest category encompassing plaques that display no elevation, no erythema, and no scale, respectively.

3. The method of claim 2 wherein the overall elevation, erythema and scale of the patient's psoriasis plaques are categorized into 2 to 8 categories of increasing severity.

4. The method of claim 3 wherein the overall elevation, erythema and scale of the patient's psoriasis plaques are categorized into 4 categories of increasing severity.

5. The method of claim 1 wherein the percent of the patient's body surface exhibiting signs of psoriasis is grouped into a plurality of percentage ranges of increasing involvement.

6. The method of claim 5 wherein the percent of the patient's body surface exhibiting signs of psoriasis is grouped into 4 to 10 ranges of increasing involvement.

7. The method of claim 5 wherein the lowest range is 0% body surface involvement and the highest range is approximately 51%-100% body surface involvement.

8. The method of claim 7 wherein the percent of the patient's body surface involvement is grouped into the following ranges:
   0% of the body surface exhibiting signs of psoriasis,
   from about 1 to about 3% of the body surface exhibiting signs of psoriasis,
   from about 4 to about 9% of the body surface exhibiting signs of psoriasis,
   from about 10 to about 20% of the body surface exhibiting signs of psoriasis,
   from about 21% to about 29% of the body surface exhibiting signs of psoriasis,
   from about 30 to about 50% of the body surface exhibiting signs of psoriasis, and
   from about 51% to 100% of the body surface exhibiting signs of psoriasis.

9. The method of claim 5, wherein the percentage ranges are broader as the percent of body surface involvement increases.

10. The method of claim 1 wherein the weight given to the overall elevation of the patient's psoriasis in classifying the severity of the patient's psoriasis into a higher class is greater than the weight given to the overall erythema or scale of the patient's psoriasis plaques.

11. The method of claim 1 wherein the weight given to the overall erythema of the patient's plaques in classifying the severity of the patient's psoriasis into a higher class is greater than the weight given to the overall scale of the patient's psoriasis plaques.

12. The method of claim 1, wherein the patient's psoriasis is classified into 5 to 8 classes of increasing severity.

13. The method of claim 1, wherein the patient's psoriasis is classified into 8 classes of increasing severity.

14. The method of claim 13, wherein the patient's psoriasis is classified into the lowest class if 0% of the patient's body surface exhibits signs of psoriasis.

15. The method of claim 13 wherein the patient's psoriasis is classified into the second class if the % of body area involved is from about 1 to about 3% and, of the overall elevation, erythema, and scale of the patient's psoriasis plaques, none is worse than the next to lowest category.

16. The method of claim 13 wherein the patient's psoriasis is classified into the third class if from about 1 to about 3% of the body surface is involved, and the overall elevation, erythema, and scale of the patient's psoriasis plaques are all in the highest or next to highest category.

17. The method of claim 13 wherein the patient's psoriasis is classified into the second class if from about 4 to about 9% of the body surface is involved, the plaques are not elevated, and the overall erythema or overall scale of the patient's psoriasis plaques are in the next to lowest category.

18. The method of claim 13 wherein the patient's psoriasis is classified into the third class if from about 4 to about 9% of the body surface is involved, and the overall elevation of the patient's psoriasis plaques is in the next to lowest category, or the overall erythema or overall scale of the patient's psoriasis plaques are in the next to highest category.

19. The method of claim 13 wherein the patient's psoriasis is classified into the fourth class if from about 4 to about 9% of the body surface is involved, and the overall elevation of the plaques is in the next to highest category or the overall scale is in the highest category.

20. The method of claim 13 wherein the patient's psoriasis is classified into the fifth class if from about 4 to about 9% of the body area is involved and the overall elevation or overall erythema of the patient's plaques are in the highest category.

21. The method of claim 13 wherein the patient's psoriasis is classified into the third class is from about 10 to about 20% of the body surface is involved, the plaques are not elevated, and the overall erythema is in the next to lowest category or the overall scale of the patient's psoriasis plaques is in the next to lowest or next to highest category.

22. The method of claim 13 wherein the patient's psoriasis is classified into the fourth class if from about 10 to about 20% of the body surface is involved, the plaques are not elevated, and the overall erythema of the patient's plaques is in the next to highest category.

23. The method of claim 13 wherein the patient's psoriasis is classified into the fifth class if from about 10 to about 20% of the body surface is involved, and the overall elevation of the patient's psoriasis plaques is in the next to lowest category.

24. The method of claim 13 wherein the patient's psoriasis is classified into the sixth class if from about 10 to about 20% of the body surface is involved, and the overall elevation of the patient's psoriasis plaques is in the next to highest category or the overall scale of the patient's plaques is in the highest category.

25. The method of claim 13 wherein the patient's psoriasis is classified into the seventh class if from about 10 to about 20% of the body surface is involved, and the overall elevation of the patient's psoriasis plaques is in the highest category or the overall erythema of the patient's plaques is in the highest category.

26. The method of claim 13 wherein the patient's psoriasis is classified into the fourth class if from about 21 to about 29% of the body surface is involved, the plaques are not elevated, and the overall erythema is in the next to lowest category or the overall scale of the patient's psoriasis plaques is in the next to lowest or next to highest category.

27. The method of claim 13 wherein the patient's psoriasis is classified into the fifth class if from about 21 to about 29% of the body surface is involved, the plaques are not elevated, and the overall erythema of the patient's plaques is in the next to highest category.

28. The method of claim 13 wherein the patient's psoriasis is classified into the sixth class if from about 20 to about 29% of the body surface is involved and the overall elevation of the patient's psoriasis plaques is in the next to lowest category.

29. The method of claim 13 wherein the patient's psoriasis is classified into the seventh class if from about 21 to about 29% of the body surface is involved, and the overall elevation is the next to highest or highest category, or the overall erythema or the overall scale of the patient's plaques is in the highest category.

30. The method of claim 13, wherein the patient's psoriasis is classified into the fifth class if from about 30 to about 50% of the body surface is involved, the plaques are not elevated, and the overall erythema or overall scale of the patient's psoriasis plaques are in the next to lowest category.

31. The method of claim 13, wherein the patient's psoriasis is classified into the sixth class if from about 30 to about 50% of the body surface is involved, the plaques are not elevated, and the overall erythema or overall scale of the patient's plaques is in the next to highest category.

32. The method of claim 13, wherein the patient's psoriasis is classified into the seventh class if from about 30 to about 50% of the patient's body surface is involved and the overall elevation of the patient's psoriasis plaques is in the next to lowest category.

33. The method of claim 13, wherein the patient's psoriasis is classified into the eighth class if from about 30 to about 50% of the body surface is involved, and the overall elevation is the next to highest or highest category, or the overall erythema or the overall scale of the patient's plaques is in the highest category.

34. The method of claim 13, wherein a patient with approximated 51% or greater body surface involved is classified as follows:
  a) into the eighth class if the patient's plaques exhibit overall any elevation or the highest category of scale or erythema;
  b) into the seventh class if the patient's plaques are not elevated and are categorized into the next to highest category erythema or scale, or
  c) into the sixth class if the patient's plaques are not elevated and are categorized into the next to lowest category for erythema or scale.

35. The method of claim 13, wherein a patient with about 21% to about 29% body surface involved is classified as follows:
  a) into the seventh class if the patient's plaques exhibit elevation of the highest or next to highest category or the highest category of scale or erythema,
  b) into the sixth class if the patient's plaques exhibit elevation of the next to lowest category or are categorized into the next to highest category for erythema, or
  c) into the fourth class if the patient's plaques are not elevated and are categorized into the next to lowest category for erythema or next to lowest or next to highest category for scale.

36. The method of claim 13, wherein a patient with about 30% to about 50% body surface involved is classified as follows:
  a) into the eighth class if the patient's plaques exhibit elevation of the next to highest or highest category or the highest category of scale or erythema,
  b) into the seventh class if the patient's plaques exhibit elevation of the next to lowest category or are categorized into the next to highest category for erythema or scale, or
  c) into the fifth class if the patient's plaques are not elevated and are categorized into the next to lowest category for erythema or scale.

37. The method of claim 13, wherein a patient with approximately 51% or greater body surface involved is classified as follows:
  a) into the eighth class if the patient's plaques exhibit overall any elevation or the highest or next to highest category of scale or erythema, or
  b) into the sixth class if the patient's plaques are not elevated and are categorized into the next to lowest category for erythema or scale.

38. The method of claim 1 where the psoriasis plaques are assessed for one or a combination of the following alternate assessments:
  thickness, induration, or infiltration instead of elevation;
  color or redness instead of erythema; and
  scaling or desquamation instead of scale.

39. The method of claim 1, wherein the level of severity is increased by 1 to 2 levels if the patient's face, groin, palms, soles, or axilla exhibit signs of psoriasis.

40. The method of claim 1, wherein the level of severity is increased by 2 to 3 levels if 2 or more of the following regions of the patient's body exhibit signs of psoriasis: face, groin, palms, soles, and axilla.

41. The method of claim 1, whereby the assessment of psoriasis is performed visually, by palpation, by instrumentation, or by other measurement such that the various qualities of psoriasis may be rated.

42. A computer readable medium for storing computer executable instructions operable to perform computer executable elements of the method of claim 1.

43. The method of claim 1 wherein the overall elevation of the patient's psoriasis plaques are categorized into a first class, a second class, a third class, or a fourth class, the assessing in b) further including:
  d) categorizing the patient's psoriasis plaques for overall elevation in the first class when, overall, there is no elevation in the psoriasis plaques above normal skin;
  e) categorizing the patient's psoriasis plaques for overall elevation in the second class when, overall, there is slight elevation in the psoriasis plaques above surrounding normal skin and edges of the psoriasis plaques are barely palpable and not visually apparent;
  f) categorizing the patient's psoriasis plaques for overall elevation in the third class when, overall, there is visually apparent elevation in edges of the psoriasis plaques and the edges are readily palpated and rounded or sloped; and
  g) categorizing the patient's psoriasis plaques for overall elevation in the fourth class when, overall, there is visually obvious elevation in edges of the psoriasis plaques and the edges are easily palpated with sharp edges providing a discernable bump.

44. The method of claim 1 wherein the overall erythema of the patient's psoriasis plaques are categorized into a first class, a second class, a third class, or a fourth class, the assessing in b) further including:
  d) categorizing the patient's psoriasis plaques for overall erythema in the first class when, overall, there is normal skin color or post-inflammatory color change in the psoriasis plaques;
  e) categorizing the patient's psoriasis plaques for overall erythema in the second class when, overall, there is pink color in the psoriasis plaques;
  f) categorizing the patient's psoriasis plaques for overall erythema in the third class when, overall, there is light to medium red color in the psoriasis plaques; and
  g) categorizing the patient's psoriasis plaques for overall erythema in the fourth class when there is bright, full, or deep red color in the psoriasis plaques.

45. The method of claim 1 wherein the overall scale of the patient's psoriasis plaques are categorized into a first class, a second class, a third class, or a fourth class, the assessing in b) further including:
- d) categorizing the patient's psoriasis plaques for overall scale in the first class when, overall, there are no scales in the psoriasis plaques:
- e) categorizing the patient's psoriasis plaques for overall scale in the second class when, overall, there are fine scales in the psoriasis plaques;
- f) categorizing the patient's psoriasis plaques for overall scale in the third class when, overall, there are discernable yellow to silver colored individual scales in the psoriasis plaques; and
- g) categorizing the patient's psoriasis plaques for overall scale in the fourth class when, overall, there are coarse or thick, yellow to silver colored scales in the psoriasis plaques and the surface is rough.

* * * * *